United States Patent
Knecht et al.

(10) Patent No.: US 6,981,957 B2
(45) Date of Patent: Jan. 3, 2006

(54) KNEE BRACE MEDIAL/LATERAL SHIFT COMPENSATION

(75) Inventors: Steven S. Knecht, Bakersfield, CA (US); Jeffrey H. Townsend, Bakersfield, CA (US)

(73) Assignee: Townsend Industries, Inc., Bakersfield, CA (US)

( * ) Notice: Subject to any disclaimer, the term of this patent is extended or adjusted under 35 U.S.C. 154(b) by 0 days.

(21) Appl. No.: 10/787,763

(22) Filed: Feb. 27, 2004

(65) Prior Publication Data

US 2005/0192523 A1    Sep. 1, 2005

(51) Int. Cl.
*A61F 5/00*    (2006.01)
(52) U.S. Cl. ............... 602/26; 602/5; 602/16; 602/23
(58) Field of Classification Search ............ 602/5, 602/16, 23, 20, 26–29
See application file for complete search history.

(56) References Cited

U.S. PATENT DOCUMENTS

| 4,773,404 | A | 9/1988 | Townsend |
| 4,890,607 | A | 1/1990 | Townsend |
| 4,953,543 | A | 9/1990 | Grim et al. |
| 5,259,832 | A | 11/1993 | Townsend et al. |
| 5,330,418 | A | 7/1994 | Townsend et al. |
| 6,203,511 | B1 * | 3/2001 | Johnson et al. ............... 602/16 |
| 6,383,156 | B1 * | 5/2002 | Enzerink et al. ............. 602/16 |
| 6,387,066 | B1 | 5/2002 | Whiteside |
| 6,875,187 | B2 | 4/2005 | Castillo |
| 2002/0183672 | A1 | 12/2002 | Enzerink et al. |
| 2003/0100854 | A1 * | 5/2003 | Rossi et al. ................... 602/16 |

* cited by examiner

Primary Examiner—Kim M. Lewis
(74) Attorney, Agent, or Firm—Nixon Peabody LLP; David S. Safran

(57) ABSTRACT

An orthopedic knee brace which will allow lateral-medial compensation to be obtained while still enabling the use of known joint mechanism which will constrain the leg to execute the correct natural movement of the knee by separating lateral-medial compensation and anterior posterior movement functions. More specifically, the present invention utilizes a pair of hinges, one of which provides for movement in a posterior-anterior plane and the other which provides for movement in a medial-lateral plane. In this way, any conventional knee joint mechanism may be employed and movement of the leg can be properly constrained to execute a prescribed motion.

12 Claims, 4 Drawing Sheets

KNEE BRACE MEDIAL/LATERAL SHIFT COMPENSATION

BACKGROUND OF THE INVENTION

1. Field of the Invention

The present invention is directed to orthopedic knee braces and particularly those designed to provide medial (varus) and lateral (valgus) compensation.

2. Description of Related Art

Published U.S. Patent Application No. 2002/0183672 A1 discloses an orthopedic knee brace with adjustable length struts. Length adjustment is achieved via a telescopic adjustment assembly but no provision is made for medial or lateral adjustment of the length adjustment mechanism cannot be used for that purpose without producing binding of the joint mechanism.

A self-aligning adjustable orthopedic knee brace is disclosed in U.S. Pat. No. 6,387,066 B1. The brace of this patent has a self-aligning polycentric joint which utilizes an apertured spherical bearing element and an annular concave seat in which the bearing element is freely rotatable so as to permit not only anterior-posterior pivoting of the femoral and tibial arms with respect to each other, but also medial-lateral relative movement. Additionally, the femoral (upper) arm has a length adjustment arrangement with an adjustment screw, the head of which is rotatably retained in the top end of the femoral arm and the other of which is threaded into the facing end an adjustment arm so that rotation of the screw either draws the adjustment arm toward femoral arm or displaces it away from it. By adjustment of the arms, the angle of inclination of femoral half of the brace can be adjusted relative to the tibial half, the spherical polycentric joint allowing for the laterally or medially directed inclination without producing binding during posterior-anterior motion. However, the problem with the use of a spheric polycentric joint is that it imparts an inherent weakness to the brace in that it is not constrained against transverse rotation, i.e., rotation in a horizontal plan, and thus allows a degree of twisting between the femur and tibia. Furthermore, a joint of this type cannot duplicate the correct natural movement of the knee, such as is obtainable by the joints as disclosed in U.S. Pat. Nos. 4,773,404; 4,890,607; 5,259,832; and 5,330,418.

SUMMARY OF THE INVENTION

Therefore, it is a primary object of the present invention to provide orthopedic knee brace which will allow lateral-medial compensation to be obtained while still enabling the use of known joint mechanism which will constrain the leg to execute the correct natural movement of the knee.

In accordance with the invention, this object is achieved by separating the lateral-medial compensation and anterior posterior movement functions. More specifically, the present invention utilizes a pair of hinges, one of which provides for movement in a posterior-anterior plane and the other which provides for movement in a medial-lateral plane. In this way, any conventional knee joint mechanism may be employed and movement of the leg can be properly constrained to execute a prescribed motion.

These and other objects, features and advantages will become apparent from the following detailed description of a preferred embodiment when viewed in conjunction with the accompanying drawings.

DETAILED DESCRIPTION OF THE INVENTION

Figure 2:
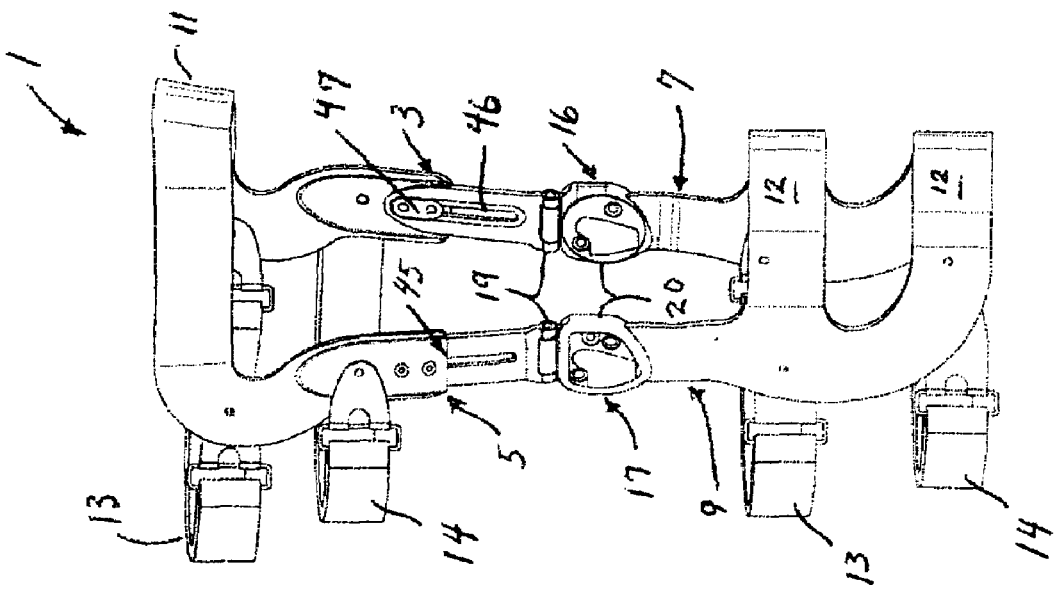
FIG. 2 is a perspective view of the knee brace shown in FIG. 1.
Figure 1:
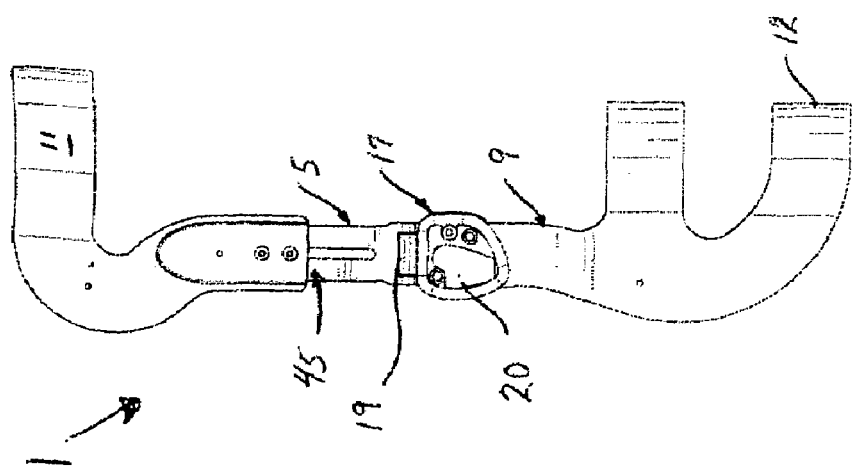
FIG. 1 is a side view of a knee brace in accordance with a preferred embodiment of the invention.

With reference to FIGS. 1 & 2, it can be seen that knee brace 1 of the present invention, as is typical, has a medial femoral arm 3 and a lateral side femoral arm 5 which are connected, respectively, to a medial tibial arm 7 and a lateral side tibial arm 9. In particular, an upper crossbar 11 connects the medial femoral arm 3 and lateral femoral arm 5 at a front side of the brace, and a pair of lower crossbars 12 connect the medial and lateral tibial arms 7, 9 at a front side of the brace. Additionally, upper and lower straps 13, 14 are provided for detachably securing the brace 1 on a leg of a user at the thigh and calf areas. In this regard, it is noted that, at least in the context of the present invention, it is important to provide at least a pair straps 13, 14 running between medial and lateral tibial arms, or other equivalent structure, in order to establish a fixed anchoring of the brace relative to the leg for reasons described more specifically below.

A medial side joint mechanism 16 couples the medial side femoral arm 3 to the medial side tibial arm 7, and a lateral side joint mechanism 17 couples the lateral side femoral arm 5 to the lateral side tibial arm 9. Each of the joint mechanisms 16, 17 comprise upper and lower hinges 19, 20, the lower hinges 20 enabling relative movement between the femoral and tibial arms in posterior-anterior planes and the upper hinges 19 enabling relative movement between the femoral and tibial arms in medial-lateral planes.

The upper hinges 19 are unicentric hinges and the lower hinges 20 are polycentric. Each of the upper hinges 19 preferably comprises a pin 22 that is engaged in pin-receiving openings 23 of the femoral arms and 24 of the joint mechanisms. While the lower hinges 20 can be of any known polycentric type, it is advantageous to use which duplicates the natural motion of the knee by providing a means for constraining the tibia to slide rearwardly relative to the femur for a predetermined distance during an initial range of flexion of the knee from a straight leg position, and beyond the initial range of flexion to, thereafter, rotate relative thereto in a predetermined arcuate path as is the case for the joints as disclosed in U.S. Pat. Nos. 4,773,404; 4,890,607; 5,259,832; and 5,330,418, all of which are hereby incorporated by reference.

Figure 3:
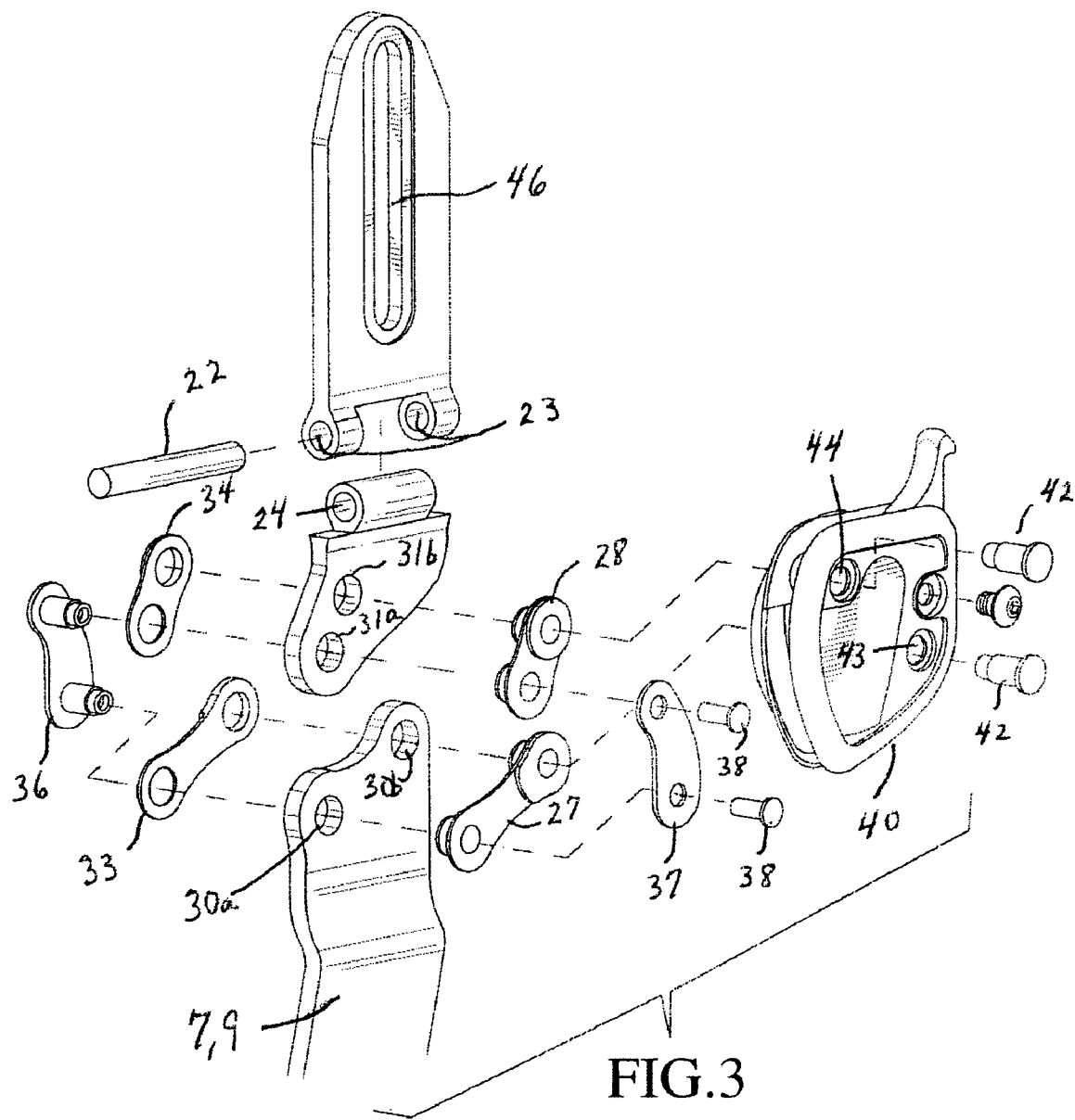
FIG. 3 is an exploded view of the joint mechanism of the FIG. 1 knee brace.
Figure 4:
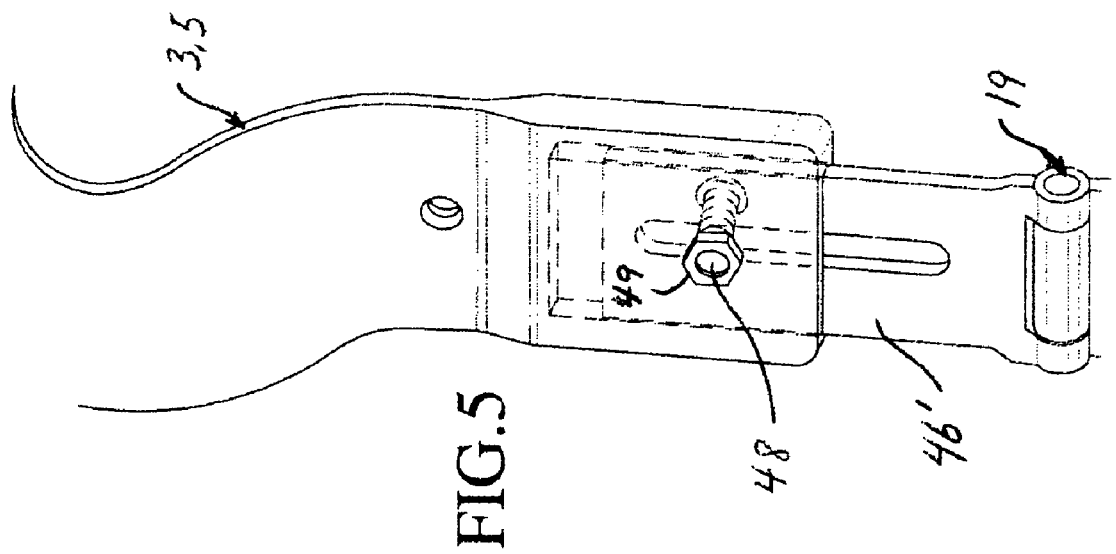
FIGS. 4 & 5 each show a perspective view of a respective version of the length adjustment mechanism of the FIG. 1 knee brace.

A lower hinge construction for the joint mechanism that is particularly advantageous is one of the type described in U.S. Pat. No. 5,259,832, which comprises a four bar linkage. With reference to FIG. 3 the four bar linkage forming the joint mechanism 17 of the preferred embodiment of the present invention will be described.

Firstly, to provide self-lubricating bearings which will also prevent, e.g., aluminum links from reacting with titanium arms, male plastic bearing elements 27, 28 are inserted into the openings 30a, 30b of the tibial arms 7, 9 and openings 31a, 31b of a lower part of the upper hinges 19, respectively. Bearing retainers 33, 34 are then snapped onto ends of the bearing elements 27, 28 which have passed through and out of the openings 30a, 30b, and 31a, 30b.

A first pivot link is formed by link elements 36, 37, which are secured together by rivets 38 after the male link element 36 has been insert through openings 30a and 31a and female link element 37 has been mounted over the ends of the link element 36 which have passed through and out of the openings 30a, 31a, thus forming first and second pivot points. Alternatively, the rivets 38 can be omitted and other fastening methods used, such as crimping of the projecting ends of the male link element 36. After attachment of the first pivot link, the hinge cover 40, which is C-shaped or clam shell-shaped, is slid over the area of the openings 30a, 30b, and 31a, 30b and the first pivot link. Then, rivets 42 are inserted into the openings 43, 44 of the hinge cover 40, through the openings 30b and 31b, and back out though the corresponding openings 43, 44 at the opposite side of the hinge cover 40, after which they are fixed in place. Thus, the portion of the hinge cover 40 between the rivets 42 constitutes the second pivot link of the four bar linkage forming the polycentric lower hinges 17 with the rivets 42 forming third and fourth pivot points.

In accordance with the concept of U.S. Pat. No. 5,259,832, an angle of intersection between an imaginary line drawn through the first and second pivot points of first pivot link and an imaginary line drawn through the third and fourth pivot points of the second pivot link is at least 24° throughout a full range of flexion from a straight leg position to a fully flexed position.

In accordance with the invention, at least one of the femoral arms 3, 5 has a length adjustment mechanism. In the case of an off the shelf (OTS) knee brace, both of the femoral arms 3, 5, would normally be provided with a length adjustment mechanism, as is the case for the knee brace 1 shown in FIG. 2. On the other hand, a custom fitted knee brace will normally require a length adjustment mechanism in only one of the femoral arms 3, 5 and the range of adjustability provided will not be as great since adjustability will be required only for fine-tuning purposes, as opposed to the case of an OTS model where it will function to a greater extent to provide a proper fit and proper medial-lateral loading, e.g., up to 1.5" of height adjustment and up to 18° of medial/lateral angular adjustment.

While various types of length adjustment mechanisms are known and may be used in accordance with the present invention, it is preferred that the length adjustment mechanism be a slide mechanism. In particular, the slide mechanism 45 illustrated in FIGS. 1–4 comprises a slotted guide 46 and a slider 47 which is fixable at selected locations along the length of the slotted guide 46 by loosening the screws 48 to free the slotted guide 46 for adjustment movement relative to the slider 47 and then re-tightening the screws 48 when the desired adjustment position has been reached. The slotted guide 46 is formed as an extension of an upper part of the upper hinge 19 of the joint mechanism 16, 17. The slotted guide 46 is received in a recess 50 that is formed in a side of a respective one of the femoral arms 3, 5. The slider 47 is a link member that is slidably received in the slot of the slotted guide 46 but is fixed relative to the respective femoral arm 3, 5 by the pair of screws 48 which are threaded into the link member and extend through the side of the respective femoral arm 3, 5 via apertures formed in the base wall of the recess 50.

Figure 5:
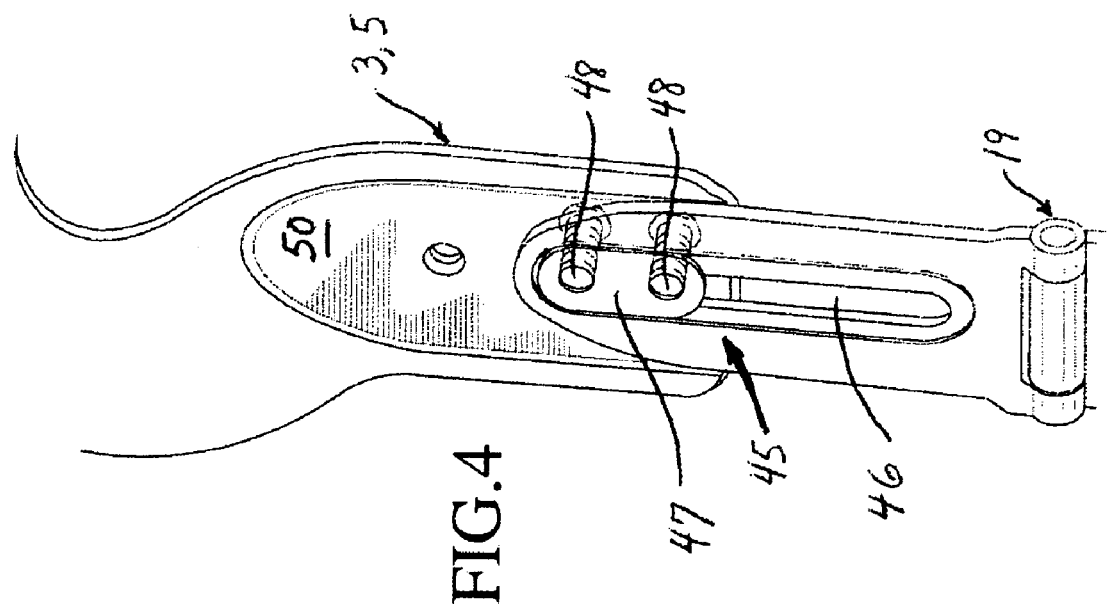

Alternatively, as shown in FIG. 5, the slotted guide 46' formed as an extension of an upper part of said joint mechanism is telescopically received within an interior space of the respective femoral arm 3, 5. In this case, the slider is only a single screw 48 is used which extends through the slot of the slotted guide 46' between and through opposite sides of the respective femoral arm. Since there is no separate slider as in the embodiment of FIG. 4, a nut 49 is threaded onto the end of the screw. Tightening of the nut on screw 48 resiliently draws the opposed walls of the hollow portion of the femoral arm 3, 5 together so as to clamp the slotted guide 46' therebetween, and loosening of the nut 49 on the screw 48 allows the opposed walls to move back to their unstressed positions, freeing the slotted guide to move in and out of the femoral arm 3, 5. This construction is particular useful for a custom fitted knee brace where a lesser degree of sliding movement is required and a more finished look may be desired given the extra cost of a custom fitted brace.

Figure 8:
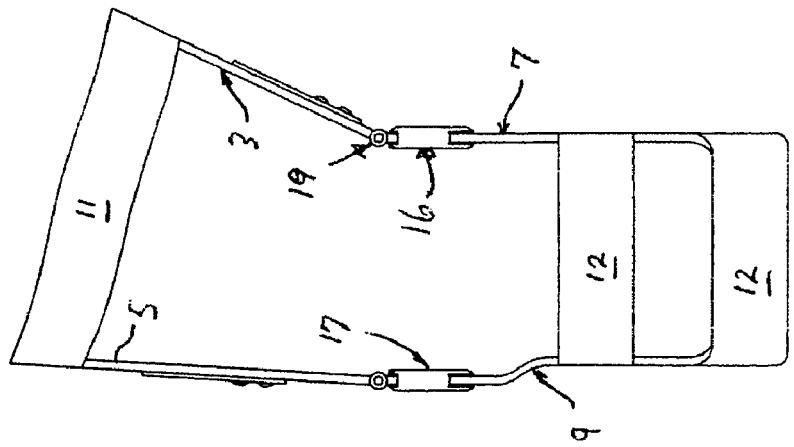
FIGS. 6–8 show the FIG. 1 knee brace in neutral, medially shifted and laterally shifted positions, respectively.
Figure 7:
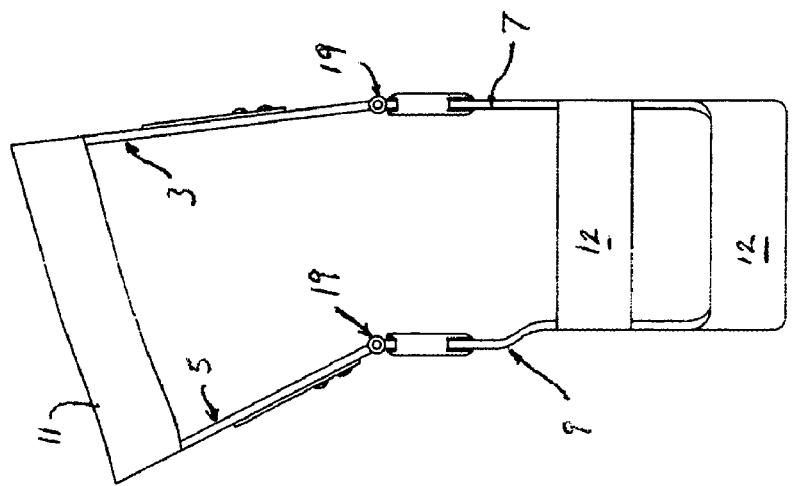
Figure 6:
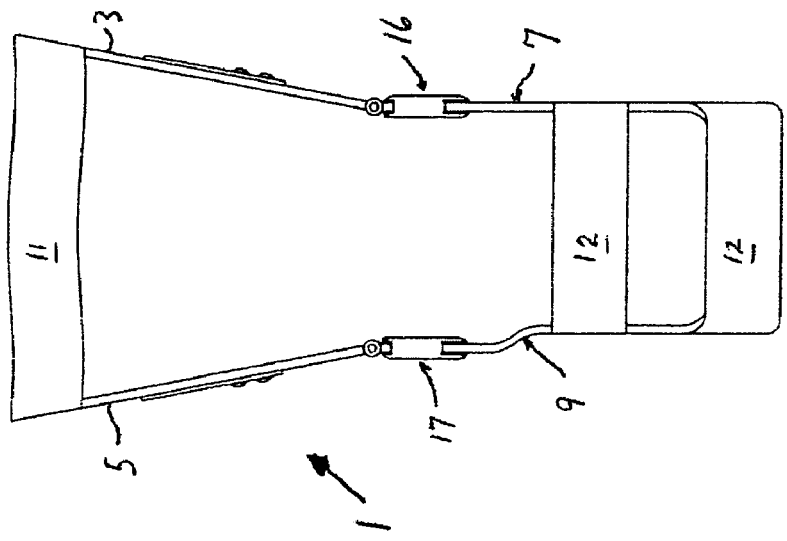

FIGS. 6–8 show examples of the operation of the length adjustment mechanisms 45 and double hinge joint mechanism of the present invention with the OTS knee brace of the invention. FIG. 6 shows the situation where both length adjustment mechanisms 45 are fully extend in a neutral angular position. FIG. 7 shows the medial side adjustment mechanism 45 maximally extended and the lateral side length adjustment mechanism 45 maximally retracted resulting in a maximally lateral angular correction of about 18°, the femoral arms 3, 5 pivoting about the unicentric hinges 19. FIG. 8 shows the lateral side adjustment mechanism 45 maximally extended and the medial side length adjustment mechanism 45 maximally retracted resulting in a maximally medial angular correction of about 18°, the femoral arms 3, 5 pivoting about the unicentric hinges 19. Because of the action of the unicentric hinges 19, lateral/medial loads that could produce binding of the polycentric hinges 16, 17, are not transmitted to the polycentric hinges so that the can move freely despite and angular corrections that are set.

FIGS. 6–8 show examples of the operation of the length adjustment mechanisms 45 and double hinge joint mechanism of the present invention with the OTS knee brace of the invention. FIG. 6 shows the situation where both length adjustment mechanisms 45 are fully extend in a neutral angular position. FIG. 7 shows the medial side adjustment mechanism 45 maximally extended and the lateral side length adjustment mechanism 45 maximally retracted resulting in a maximally lateral angular correction of about 18°, the femoral arms 3, 5 pivoting about the unicentric hinges 19. FIG. 8 shows the lateral side adjustment mechanism 45 maximally extended and the medial side length adjustment mechanism 45 maximally retracted resulting in a maximally medial angular correction of about 18°, the femoral arms 3, 5 pivoting about the unicentric hinges 19. Because of the action of the unicentric hinges 19, lateral/medial loads that could produce binding of the polycentric hinges 16, 17, are not transmitted to the polycentric hinges so that they can move freely despite any angular corrections that are set.

While preferred embodiments of the invention have been shown and described, it should be appreciated that the invention is not limited to the specifics of these embodiments. To the contrary, numerous variations and modifications within the scope of the disclosed concepts will be apparent to those of ordinary skill, e.g, through the use of different types of hinge mechanisms, different types of adjustment mechanisms and different manners for attachment of the brace to a wearer's leg, as well as the provision of various ancillary features, such as angular adjustment stops. As such, the invention should be considered as being fully commensurate with the scope of the appended claims.

What is claimed is:

1. A knee brace, comprising:
   a medial and a lateral side femoral arm;
   a medial and a lateral side tibial arm;
   a medial side joint mechanism coupling the medial side femoral arm to the medial side tibial arm;
   a lateral side joint mechanism coupling the medial side femoral arm to the lateral side tibial arm;
   wherein each of said medial side joint mechanism and said lateral side joint mechanism comprise upper and lower hinges, the lower hinges enabling relative movement between the femoral arms and the tibial arms in posterior-anterior planes and the upper hinges enabling free relative movement between the femoral arms and the tibial arms in medial-lateral planes; and
   wherein at least one of said femoral arms has a length adjustment mechanism; and wherein adjustment of the length of one of the arms produces a medial-lateral angular movement of at least one or the other of the femoral arms about said upper hinges.

2. Knee brace according to claim 1, wherein the upper hinges are unicentric hinges and the lower hinges are polycentric.

3. Knee brace according to claim 2, wherein each of the upper hinges comprise a pin engaged in pin-receiving openings of the femoral arms and the joint mechanisms.

4. Knee brace according to claim 2, wherein each of the lower hinges comprise means for constraining the tibia to slide rearwardly relative to the femur for a predetermined distance during an initial range of flexion of the knee from a straight leg position and, beyond said initial range of flexion to, thereafter, rotate relative thereto in a predetermined arcuate path.

5. Knee brace according to claim 4, wherein each of the lower hinges comprises a four bar linkage having a first pivot link pivotally connected at a first pivot point to a respective one of said tibial arms and at a second pivot point to a respective one of said upper hinges, and a second pivot link, pivotally connected at a third pivot point to a respective one of said tibial arms and at a fourth pivot point to a respective one of said upper hinges; and wherein an angle of intersection between an imaginary line drawn through said first and second pivot points and an imaginary line drawn through said third and fourth pivot points is at least 24 degrees throughout a full range of flexion from a straight leg position to a fully flexed position.

6. Knee brace according to claim 1, wherein each of the lower hinges comprise means for constraining the tibia to slide rearwardly relative to the femur for a predetermined distance during an initial range of flexion of the knee from a straight leg position and, beyond said initial range of flexion to, thereafter, rotate relative thereto in a predetermined arcuate path.

7. Knee brace according to claim 6, wherein each of the lower hinges comprises a four bar linkage having a first pivot link pivotally connected at a first pivot point to a respective one of said tibial arms and at a second pivot point to a respective one of said upper hinges, and a second pivot link, pivotally connected at a third pivot point to a respective one of said tibial arms and at a fourth pivot point to a respective one of said upper hinges; and wherein an angle of intersection between an imaginary line drawn through said first and second pivot points and an imaginary line drawn through said third and fourth pivot points is at least 24 degrees throughout a full range of flexion from a straight leg position to a fully flexed position.

8. Knee brace according to claim 1, further comprising an upper crossbar connecting the medial and lateral femoral arms at a front side of the brace, a pair of lower crossbars connecting the medial and lateral tibial arms at a front side of the brace, and upper and lower strap means for detachably securing the brace on a leg of user, said lower strap means comprising a strap running between medial and lateral end areas of each said lower crossbars at a rear side of said brace.

9. Knee brace according to claim 1, wherein said length adjustment mechanism on at least one of said femoral arms is a slide mechanism.

10. Knee brace according to claim 9, wherein said slide mechanism comprises a slotted guide and a slider which is fixable at selected locations along the length of said slotted guide.

11. Knee brace according to claim 10, wherein said slotted guide is formed as an extension of an upper part of said joint mechanism which is telescopically received within an interior space of a respective one of the femoral arms, and wherein said slider is a screw extending through the slot of the slotted guide between opposite sides of the respective femoral arm.

12. Knee brace according to claim 10, wherein said slotted guide is formed as an extension of an upper part of said joint mechanism which is received in a recess formed in a side of a respective one of the femoral arms: wherein said slider is a link member that is slidably received in the slot of the slotted guide; and wherein a pair of screws extend through the link member between opposite sides of the respective femoral arm.

* * * * *